United States Patent
Birgisdottir et al.

(10) Patent No.: US 11,510,793 B2
(45) Date of Patent: Nov. 29, 2022

(54) ADJUSTABLE SEAL SYSTEM, SEAL COMPONENT AND METHOD FOR USING THE SAME

(71) Applicant: OSSUR ICELAND EHF, Reykjavik (IS)

(72) Inventors: Linda Ros Birgisdottir, Reykjavik (IS); Martin Lund Storup, Reykjavik (IS); Hogna Hringsdottir, Reykjavik (IS); Rowan Cain, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 467 days.

(21) Appl. No.: 16/198,427

(22) Filed: Nov. 21, 2018

(65) Prior Publication Data

US 2019/0159911 A1    May 30, 2019

Related U.S. Application Data

(60) Provisional application No. 62/591,502, filed on Nov. 28, 2017.

(51) Int. Cl.
*A61F 2/78* (2006.01)
*A61F 2/80* (2006.01)

(52) U.S. Cl.
CPC .............. *A61F 2/7812* (2013.01); *A61F 2/80* (2013.01); *A61F 2002/785* (2013.01);
(Continued)

(58) Field of Classification Search
CPC .. A61F 2/78; A61F 2/7812; A61F 2/80; A61F 2002/7837
See application file for complete search history.

(56) References Cited

U.S. PATENT DOCUMENTS

| | | |
|---|---|---|
| 980,457 A | 1/1911 | Toles |
| 1,398,824 A | 11/1921 | Abrams |

(Continued)

FOREIGN PATENT DOCUMENTS

| | | |
|---|---|---|
| AT | 369 978 B | 2/1983 |
| DE | 484 363 C | 10/1929 |

(Continued)

OTHER PUBLICATIONS

International Search Report and Written Opinion from PCT Application No. PCT/US2018/058624, dated Feb. 11, 2019.
(Continued)

*Primary Examiner* — Marcia L Watkins
(74) *Attorney, Agent, or Firm* — Workman Nydegger

(57) ABSTRACT

An adjustable seal system includes a seal component having a body having an outer surface defining a socket sealing portion arranged to engage and form an airtight seal with an interior surface of a prosthetic socket. The inner surface of the body defines a liner sealing portion arranged to frictionally engage and seal with an outer surface of a prosthetic liner. The liner sealing portion defines a sealing length extending in a proximal direction from an end of the socket sealing portion and terminating at a proximal edge on the body. The length of the liner sealing portion is between about 25 mm and about 35 mm and is selected in relation to the socket sealing portion to vary tractions at the inner and outer surfaces of the seal component.

11 Claims, 6 Drawing Sheets

(52) U.S. Cl.
CPC . *A61F 2002/7837* (2013.01); *A61F 2002/802* (2013.01); *A61F 2002/805* (2013.01)

(56) References Cited

U.S. PATENT DOCUMENTS

| | | | |
|---|---|---|---|
| 1,893,853 A | 1/1933 | Tullis | |
| 2,244,871 A | 6/1941 | Guinzburg | |
| 2,325,656 A | 8/1943 | Brophy | |
| 2,464,443 A | 3/1949 | Ganoe et al. | |
| 2,530,285 A | 11/1950 | Catranis | |
| 2,533,404 A | 12/1950 | Sharp et al. | |
| 2,634,424 A | 4/1953 | O'Gorman | |
| 2,671,225 A | 3/1954 | Schoene et al. | |
| 2,689,351 A | 9/1954 | Schindler | |
| 2,808,593 A | 10/1957 | Andersen | |
| 3,393,407 A | 7/1968 | Kandel | |
| 3,587,572 A | 6/1971 | Evans | |
| 3,671,980 A | 6/1972 | Baird | |
| 3,947,897 A | 4/1976 | Owens | |
| 4,128,903 A | 12/1978 | Marsh et al. | |
| 4,215,679 A | 8/1980 | Rustin | |
| 4,311,317 A | 1/1982 | Bartels | |
| 4,319,413 A | 3/1982 | Mattil | |
| 4,347,204 A | 8/1982 | Takagi et al. | |
| 4,474,573 A | 10/1984 | Detty | |
| 4,635,626 A | 1/1987 | Lerman | |
| 4,738,249 A | 4/1988 | Linman et al. | |
| 4,767,735 A | 8/1988 | Ewen et al. | |
| 4,885,828 A | 12/1989 | Kozlowski | |
| 4,908,037 A | 3/1990 | Ross | |
| 4,923,474 A | 5/1990 | Klasson et al. | |
| 5,007,937 A | 4/1991 | Fishman et al. | |
| 5,055,528 A | 10/1991 | Kioka et al. | |
| 5,108,456 A | 4/1992 | Coonan, III | |
| 5,122,583 A | 6/1992 | Ewen et al. | |
| 5,139,523 A | 8/1992 | Paton et al. | |
| 5,163,965 A | 11/1992 | Rasmusson et al. | |
| 5,169,161 A | 12/1992 | Jones | |
| 5,226,918 A | 7/1993 | Silagy et al. | |
| 5,244,716 A | 9/1993 | Thornton et al. | |
| 5,314,496 A | 5/1994 | Harris et al. | |
| 5,376,129 A | 12/1994 | Faulkner et al. | |
| 5,376,131 A | 12/1994 | Lenze et al. | |
| 5,387,245 A | 2/1995 | Fay et al. | |
| 5,549,709 A | 8/1996 | Caspers | |
| 5,571,208 A | 11/1996 | Caspers | |
| 5,571,209 A | 11/1996 | Brown, Sr. | |
| 5,593,454 A | 1/1997 | Helmy | |
| 5,658,353 A | 8/1997 | Layton | |
| 5,702,489 A | 12/1997 | Slemker | |
| 5,718,925 A | 2/1998 | Kristinsson et al. | |
| 5,728,168 A | 3/1998 | Laghi et al. | |
| 5,728,170 A | 3/1998 | Becker et al. | |
| 5,735,906 A | 4/1998 | Caspers | |
| 5,830,237 A | 11/1998 | Kania | |
| 5,885,674 A | 3/1999 | Maemoto et al. | |
| 5,888,216 A | 3/1999 | Haberman | |
| 5,888,230 A | 3/1999 | Helmy | |
| 5,904,722 A | 5/1999 | Caspers | |
| 5,931,872 A | 8/1999 | Lohmann | |
| 5,972,036 A | 10/1999 | Kristinsson et al. | |
| 5,980,577 A | 11/1999 | Radis et al. | |
| 6,076,284 A | 6/2000 | Terlizzi | |
| 6,136,039 A | 10/2000 | Kristinsson et al. | |
| 6,149,691 A | 11/2000 | Fay et al. | |
| 6,171,431 B1 | 1/2001 | Gallagher, Jr. et al. | |
| 6,231,616 B1 | 5/2001 | Helmy | |
| 6,231,617 B1 | 5/2001 | Fay | |
| 6,273,918 B1 | 8/2001 | Yuhasz et al. | |
| 6,287,345 B1 | 9/2001 | Slemker et al. | |
| 6,361,568 B1 | 3/2002 | Hoerner | |
| 6,368,357 B1 | 4/2002 | Schon et al. | |
| 6,406,499 B1 | 6/2002 | Kania | |
| 6,468,938 B1 | 10/2002 | Govoni et al. | |
| 6,485,776 B2 | 11/2002 | Janusson et al. | |
| 6,508,842 B1 | 1/2003 | Caspers | |
| 6,544,292 B1 | 4/2003 | Laghi | |
| 6,554,868 B1 | 4/2003 | Caspers | |
| 6,585,774 B2 | 7/2003 | Dean, Jr. et al. | |
| 6,592,539 B1 | 7/2003 | Einarsson et al. | |
| 6,626,952 B2 | 9/2003 | Janusson et al. | |
| 6,645,253 B2 | 11/2003 | Caspers | |
| 6,706,364 B2 | 3/2004 | Janusson et al. | |
| 6,726,726 B2 | 4/2004 | Caspers | |
| 6,761,742 B2 | 7/2004 | Caspers | |
| 6,797,008 B1 | 9/2004 | Arbogast et al. | |
| 6,852,269 B2 | 2/2005 | Eberle et al. | |
| 6,926,742 B2 | 8/2005 | Caspers et al. | |
| 6,929,125 B1 | 8/2005 | Seamans | |
| 6,964,688 B1 | 11/2005 | Kania | |
| 7,001,563 B2 | 2/2006 | Janusson et al. | |
| 7,025,793 B2 | 4/2006 | Egilsson | |
| 7,118,602 B2 | 10/2006 | Bjarnason | |
| 7,144,429 B2 | 12/2006 | Carstens | |
| 7,169,188 B2 | 1/2007 | Carstens | |
| 7,169,189 B2 | 1/2007 | Bjarnason et al. | |
| 7,235,108 B2 | 6/2007 | Carstens | |
| 7,291,182 B1 | 11/2007 | Kania | |
| 7,351,264 B2 | 4/2008 | Wilson | |
| 7,427,297 B2 | 9/2008 | Patterson et al. | |
| 7,592,286 B2 | 9/2009 | Morini et al. | |
| 7,749,281 B2 | 7/2010 | Egilsson | |
| 7,771,487 B2 | 8/2010 | Mantelmacher | |
| 7,909,884 B2 | 3/2011 | Egilsson et al. | |
| 8,034,120 B2 | 10/2011 | Egilsson et al. | |
| 8,052,760 B2 | 11/2011 | Egilsson et al. | |
| 8,097,043 B2 | 1/2012 | Egilsson | |
| 8,206,459 B1 | 6/2012 | Lock et al. | |
| 8,372,159 B2 | 2/2013 | Mackenzie | |
| 8,911,506 B2 | 12/2014 | Egilsson et al. | |
| 9,060,885 B2 | 6/2015 | Egilsson et al. | |
| 9,066,821 B2 | 6/2015 | Egilsson et al. | |
| 9,603,726 B2 | 3/2017 | Egilsson et al. | |
| 9,707,106 B2 | 7/2017 | Egilsson et al. | |
| 2001/0005798 A1 | 6/2001 | Caspers | |
| 2001/0016781 A1 | 8/2001 | Caspers | |
| 2002/0040248 A1 | 4/2002 | Karason | |
| 2002/0087215 A1 | 7/2002 | Caspers | |
| 2002/0091449 A1 | 7/2002 | Caspers et al. | |
| 2002/0099450 A1 | 7/2002 | Dean, Jr. et al. | |
| 2002/0165619 A1 | 11/2002 | Hellberg | |
| 2002/0183859 A1 | 12/2002 | Houser | |
| 2003/0181989 A1 | 9/2003 | Eberle et al. | |
| 2003/0191539 A1 | 10/2003 | Caspers | |
| 2004/0012158 A1 | 1/2004 | Neuhaus | |
| 2004/0024322 A1 | 2/2004 | Caspers | |
| 2004/0030411 A1 | 2/2004 | Caspers | |
| 2004/0040248 A1 | 3/2004 | Vilnes | |
| 2004/0098136 A1 | 5/2004 | Caspers | |
| 2004/0122528 A1 | 6/2004 | Egilsson | |
| 2004/0143345 A1 | 7/2004 | Caspers | |
| 2004/0167638 A1 | 8/2004 | Caspers | |
| 2004/0181290 A1 | 9/2004 | Caspers | |
| 2004/0236434 A1 | 11/2004 | Carstens | |
| 2004/0243251 A1 | 12/2004 | Carstens | |
| 2004/0243252 A1 | 12/2004 | Carstens | |
| 2005/0101693 A1 | 5/2005 | Arbogast et al. | |
| 2005/0216095 A1 | 9/2005 | Egilsson | |
| 2005/0240282 A1 | 10/2005 | Rush et al. | |
| 2005/0240283 A1 | 10/2005 | Kania | |
| 2005/0267598 A1 | 12/2005 | Bjarnason et al. | |
| 2005/0267599 A1 | 12/2005 | Bjarnason | |
| 2006/0212128 A1 | 9/2006 | Nachbar | |
| 2006/0293762 A1 | 12/2006 | Schulman et al. | |
| 2007/0005149 A1 | 1/2007 | Egilsson et al. | |
| 2007/0021295 A1 | 1/2007 | Morini et al. | |
| 2007/0027556 A1 | 2/2007 | Wilson | |
| 2007/0043450 A1 | 2/2007 | Pickering et al. | |
| 2007/0061017 A1 | 3/2007 | Wilson | |
| 2007/0123998 A1 | 5/2007 | Egilsson et al. | |
| 2007/0179606 A1 | 8/2007 | Huyghe et al. | |
| 2008/0089218 A1 | 4/2008 | Egilsson | |
| 2008/0147202 A1 | 6/2008 | Danzig et al. | |
| 2008/0188949 A1 | 8/2008 | Mackenzie | |

(56) References Cited

U.S. PATENT DOCUMENTS

| | | |
|---|---|---|
| 2008/0221705 A1 | 9/2008 | Scussel |
| 2008/0221706 A1 | 9/2008 | Scussel et al. |
| 2008/0269914 A1 | 10/2008 | Coppens et al. |
| 2009/0036999 A1 | 2/2009 | Egilsson et al. |
| 2009/0069171 A1 | 3/2009 | Sagae |
| 2009/0157196 A1 | 6/2009 | Danzig et al. |
| 2009/0182435 A1 | 7/2009 | Haberman |
| 2009/0198346 A1 | 8/2009 | Perkins et al. |
| 2009/0240344 A1 | 9/2009 | Colvin et al. |
| 2009/0306791 A1 | 12/2009 | Slemker et al. |
| 2010/0070051 A1 | 3/2010 | Carstens |
| 2010/0185300 A1 | 7/2010 | Mackenzie |
| 2010/0249950 A1 | 9/2010 | Bielefeld |
| 2010/0274364 A1 | 10/2010 | Pacanowsky et al. |
| 2010/0318196 A1 | 12/2010 | Egilsson |
| 2011/0029096 A1 | 2/2011 | Laghi |
| 2011/0035027 A1 | 2/2011 | Mccarthy |
| 2011/0054635 A1 | 3/2011 | Watts |
| 2011/0071649 A1 | 3/2011 | Mckinney |
| 2011/0077748 A1 | 3/2011 | Egilsson et al. |
| 2011/0118854 A1 | 5/2011 | Halldorsson |
| 2012/0041568 A1 | 2/2012 | Mackenzie |
| 2012/0095571 A1 | 4/2012 | Gunnarsson et al. |
| 2013/0053982 A1 | 2/2013 | Halldorsson |
| 2013/0138224 A1 | 5/2013 | Mackenzie |
| 2013/0197670 A1 | 8/2013 | Mackenzie |
| 2013/0331952 A1 | 12/2013 | Halldorsson et al. |
| 2014/0058529 A1* | 2/2014 | Schober ............... A61F 2/7812 623/36 |
| 2015/0142132 A1* | 5/2015 | Egilsson ................. A61F 2/80 623/35 |
| 2015/0142133 A1 | 5/2015 | Egilsson et al. |
| 2015/0202060 A1 | 7/2015 | Muller et al. |
| 2017/0105853 A1 | 4/2017 | Jonsson et al. |
| 2017/0304085 A1 | 10/2017 | Kurth |

FOREIGN PATENT DOCUMENTS

| | | |
|---|---|---|
| DE | 745 981 C | 5/1944 |
| DE | 813 190 C | 9/1951 |
| DE | 1 795 809 U | 9/1959 |
| DE | 2 060 239 A1 | 6/1972 |
| DE | 2 127 269 A1 | 12/1972 |
| DE | 2 540 138 A1 | 3/1977 |
| DE | 2 544 446 A1 | 4/1977 |
| DE | 3 221 920 A1 | 4/1983 |
| DE | 3 508 919 A1 | 9/1986 |
| DE | 9 419 208 U1 | 1/1995 |
| EP | 0 631 765 A1 | 1/1995 |
| EP | 1 572 043 A2 | 9/2005 |
| EP | 2353550 A1 | 8/2011 |
| EP | 2745807 A1 | 6/2014 |
| EP | 2815728 A1 | 12/2014 |
| FR | 2 420 335 A1 | 10/1979 |
| FR | 2 539 616 A1 | 7/1984 |
| FR | 2 828 093 A1 | 2/2003 |
| GB | 263 377 A | 12/1926 |
| GB | 267 988 A | 3/1927 |
| GB | 269606 A | 4/1927 |
| GB | 826 041 A | 12/1959 |
| GB | 2 069 847 A | 9/1981 |
| GB | 2 087 727 A | 6/1982 |
| JP | H0623406 A | 2/1994 |
| JP | H07109314 A | 4/1995 |
| JP | H7-155343 A | 6/1995 |
| JP | H9-104714 A | 4/1997 |
| JP | 2637076 B2 | 8/1997 |
| JP | 2740503 B2 | 4/1998 |
| JP | H10-182740 A | 7/1998 |
| JP | 2001-055413 A | 2/2001 |
| JP | 2002-500697 A | 1/2002 |
| JP | 2006-176565 A | 7/2006 |
| JP | 2006-316160 A | 11/2006 |
| JP | 2006-528271 A | 12/2006 |
| JP | 3984304 B2 | 10/2007 |
| JP | 2011206118 A | 10/2011 |
| WO | 97/34548 A2 | 9/1997 |
| WO | 00/74611 A2 | 12/2000 |
| WO | 01/54631 A1 | 8/2001 |
| WO | 01/67842 A1 | 9/2001 |
| WO | 02/26158 A2 | 4/2002 |
| WO | 03/024367 A2 | 3/2003 |
| WO | 03/024370 A1 | 3/2003 |
| WO | 03/039398 A2 | 5/2003 |
| WO | 03/099173 A1 | 12/2003 |
| WO | 2004/060136 A2 | 7/2004 |
| WO | 2010/085336 A1 | 7/2010 |
| WO | 2013/005735 A1 | 1/2013 |
| WO | 2015073793 A1 | 5/2015 |

OTHER PUBLICATIONS

"Slick SIL LSR," Surface Solutions Group LLC, retrieved from www.surfacesolutionsgroup.com on Mar. 30, 2017, 1 Page.

International Search Report from PCT Application No. PCT/US2017/029063, dated Jul. 21, 2017.

"Silicone-Only Suspension (SOS) with Socket-Loc and the Ring for the Lower Limb", found at, http://www.oandp.org/ipo/library/1995_01_002.asp. Journal of Prosthetics and Orthotics 1995;vol. 7, No. 1, p. 2.

Iceross Comfort Locking/Cushion Product Information Brochure, Mar. 27, 2009, 3 Pages.

Iceross Dermo, Product Information Sheets from Internet, http://www.ossur.com/prosthetics/liners/dermo, Mar. 27, 2009, 2 Sheets.

Military inStep: Prosthetic Socks and Liners, Product Information Sheets from Internet, http://www.amputee-coalition.org/military-instep/prosthetic-socks, Mar. 27, 2009, 3 Pages.

Prosthetic & Orthotic Update NewsLetter, No. 32, Internet Search Conducted Mar. 27, 2009, 4 Pages.

Walopur Platilon U, Product Information Brochure of Epurex Films GmbH & Co., KG, Internet Search Result Conducted Mar. 27, 2009, 2 Pages.

International Search Report and Written Opinion Issued in PCT/US2012/051645, dated Dec. 3, 2012.

Supplementary EP Search Report from EP Application No. 07837275.2, dated Feb. 19, 2014, 6 pages.

Extended European Search Report from EP Application No. 14161004.8, dated May 22, 2014, 6 pages.

Extended European Search Report from Corresponding Application No. 14163512.8, dated Jul. 30, 2014.

ESP Opti-Seal, Product Installation Instructions, http://www.wearesp.com, Downloaded Dec. 12, 2014, 1 page.

ESP Opti-Seal, "The Most Versatile Suspension System Availiable", www.wearesp.com, Downloaded Dec. 12, 2014, 2 pages.

ESP Secure-Ring System (SRS), http://www.wearesp.com, Downloaded Dec. 12, 2014, 1 page.

ESP Secure-Ring System (SRS), Product Instructions Sheet, http://www.wearesp.com, downloaded Dec. 12, 2014, 2 pages.

International Search Report from PCT Application No. PCT/US2016/055269, dated Jan. 4, 2017.

Eshraghi et al., "Gait Biomechanics of Individuals with Transtibial Amputation: Effect of Suspension System", PLOS One, vol. 9, Issue 5, May 2014, 12 Pages.

Eshraghi et al., "Pistoning Assessment in Lower Limb Prosthetic Sockets", Prosthetics and Orthotics International, vol. 36, No. 1, 2012, pp. 15-24.

Gholizadeh et al., "Transtibial Prosthesis Suspension Systems: Systematic Review of Literature", Clinical Biomechanics vol. 29, 2014, pp. 87-97.

"Prosthetics Product Catalogue", Medi Prosthetics, www.medi-prosthetics.com, Jan. 2016, 184 pages.

"Verwendung und Verklebung Des LITE Vakuum-Ringes 5W700: Usage and Gluing of the 5W700 LITE Vacuum Ring", Wagner Polymertechnik GMBH, Sep. 6, 2016, 4 Pages.

* cited by examiner

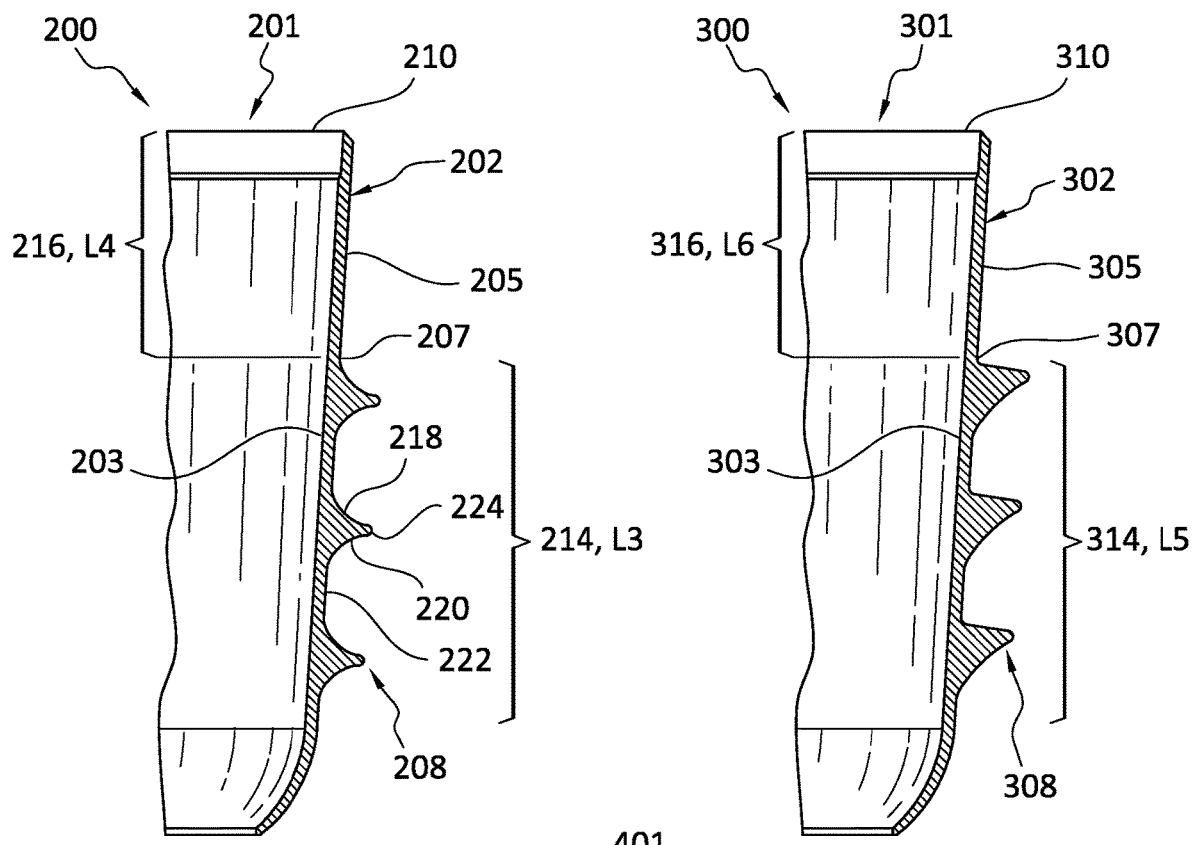
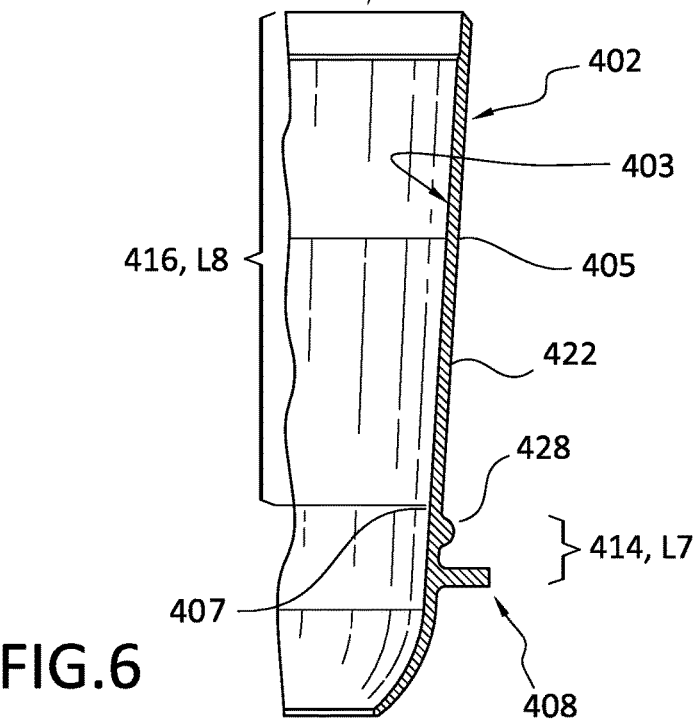

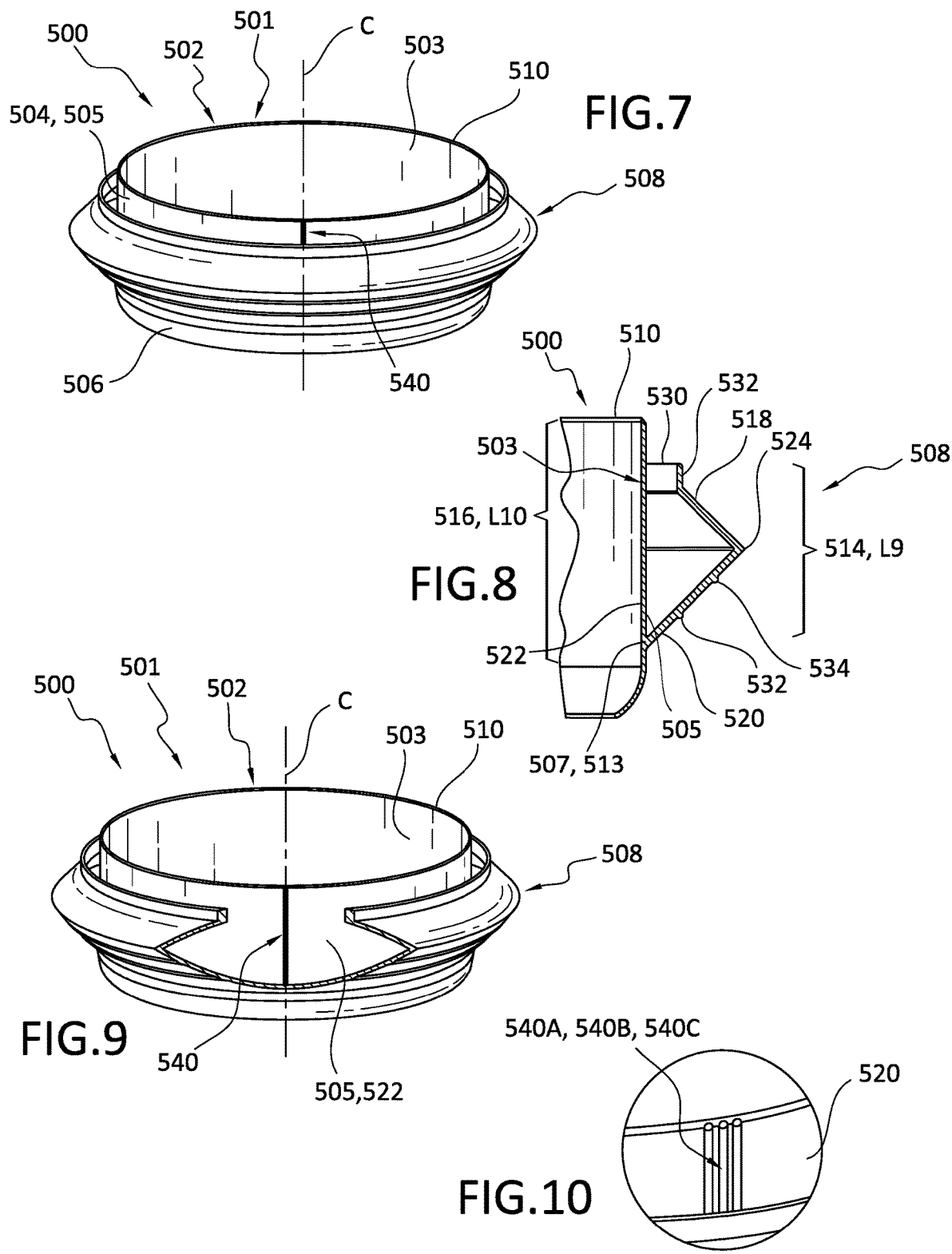

ADJUSTABLE SEAL SYSTEM, SEAL COMPONENT AND METHOD FOR USING THE SAME

TECHNICAL FIELD

This disclosure relates to suspension liners adapted to provide an interface between a residual limb and a prosthetic socket. The disclosure provides various embodiments of an adjustable seal system, seal components for use in the adjustable seal system, and methods for providing a sealing interface between a residual limb and a prosthetic socket.

BACKGROUND

In certain existing prosthetic systems, including vacuum-type suspension systems, prosthetic liners may function to secure a residual limb within a prosthetic socket as the residual limb and the prosthetic liner are inserted into the socket in a close-fitting relationship, by isolating the distal end area of the hard socket from the atmosphere. Upon application of a pulling force on the prosthetic liner relative to the socket, suction is created in the isolated distal end of the socket, the section tending to retain the prosthetic liner within the socket. Appropriate devices are usually provided to enable expulsion of air between the distal end of the liner and the hard socket, and to isolate the distal end of the hard socket member from the atmosphere after the prosthetic liner with a residual limb has been fully inserted within the socket.

In other applications, it may be desired to more positively secure the prosthetic liner within the socket by creating a hypobaric (vacuum) pressure within the distal end of the hard socket in a space defined between such distal end and the distal end of a prosthetic liner inserted into the socket with a residual limb contained within the prosthetic liner. The hypobaric pressure may be maintained at the distal end of the hard socket and the interior of the socket at its distal end will be isolated from atmosphere during normal retention of the sleeve liner within the socket. Opening the distal end of the socket to atmosphere releases the vacuum or hypobaric pressure within the socket to enable simple and easy withdrawal of a residual limb with a prosthetic liner thereon from the socket. A pump or other device may be utilized to evacuate the distal end of the socket between the distal end of a prosthetic liner and the distal end of a socket. A valve or other appropriate device typically is used to open and close the distal end of a socket to surrounding atmosphere.

Various arrangements are known in certain existing prosthetic systems for providing a seal between the exterior of the prosthetic liner and the interior of the hard socket, the seal functioning to define a suspension chamber within the socket which is separated from atmospheric pressure, including a separate and movable seal positionable on the exterior of the prosthetic liner. These movable seals allow users to selectively position the movable seal on the exterior of the liner to a desired longitudinal position to avoid sensitive or compromised tissue and may also help users who experience volume changes during the day to maintain suspension.

Disadvantageously, however, these movable seals are also prone to undesirably migrate or move circumferentially or longitudinally between the prosthetic liner and the hard socket during use. This can create the potential for failure of the suspension of the residual limb. It also can result in relative movement between the liner and the hard socket, which, in turn, reduces user comfort and increases the likelihood of friction-related injuries such as friction blisters and skin irritation. Additionally, movable seals often overcompensate for unwanted movement by being so large and/or difficult to move that a user cannot effectively don and doff the moveable seal. Such overcompensated seals often create pressure points on the residual limb, reducing comfort.

Accordingly, there is a need for an adjustable seal system with an improved seal component that allows for stable placement of the seal component on the liner, effective suspension of a residual limb within a socket, and flexibility in placement of the seal component.

SUMMARY

Embodiments of the present disclosure can include an adjustable seal component having a body having an outer surface defining a socket sealing portion arranged to engage with and form an airtight seal with an interior surface of a prosthetic socket. The inner surface of the body defines a liner sealing portion arranged to frictionally engage and seal with an outer surface of a prosthetic liner. The liner sealing portion defines a sealing length extending in a proximal direction from an end of the socket sealing portion and terminating at a proximal edge on the body. The sealing length of the liner sealing portion is between about 25 mm and about 35 mm and is selected in relation to the socket sealing portion to vary tractions at the inner and outer surfaces of the seal component.

This sealing length of the liner sealing portion can provide an amount of traction along the inner surface of the adjustable seal component that can substantially maintain the position of the adjustable seal component on the prosthetic liner when a typical amount of traction for suspending the residual limb within the prosthetic socket is present along the socket sealing portion, reducing the likelihood of undesirable migration of the adjustable seal component and thereby improving the reliability of the attachment formed by the adjustable seal component between the prosthetic liner and the prosthetic socket.

This sealing length of the liner sealing portion is also not too concentrated such as would form pressure points on a residual limb, improving user comfort. It is also not too great or extensive in length, reducing the likelihood of the traction along the liner sealing portion overcoming the amount of traction along the socket sealing portion, improving the reliability of the attachment formed by the adjustable seal component between the prosthetic liner and the socket. Additionally, this sealing length is not too great or extensive such as would make manual movement of the seal component on the prosthetic liner by a user too difficult, facilitating donning and doffing of the adjustable seal component.

According to a variation, the socket sealing portion is defined by a plurality of seal elements and a plurality of grip rings formed on the body and extending circumferentially about the outer surface of the body between the seal elements. The grip rings can be configured to enhance traction between the seal components and the interior of the socket.

According to a variation, the socket sealing portion is defined by at least one seal element spaced by a clearance from the outer surface of the body. One or more raised portions are radially positioned between the at least one seal element and a body profile of the outer surface of the body.

The one or more raised portions are configured such when the seal element is compressed against the body (closing the variable space toward the body profile) the seal element engages with the one or more raised portions before reaching the body profile, maintaining at least a portion of the seal element a distance from the body profile.

This distancing or spacing of the seal element from the body profile provided by the raised portions can create channels between the body and the seal element for permitting airflow therebetween. This advantageously reduces the risk of the seal element sticking or becoming struck on the body profile, which can undesirably restrict movement of the seal element relative to the body and can compromise the seal formed by the seal element against the interior surface of the socket, especially during use. The one or more raised portions can thus help increase the amount of traction along the socket sealing portion and/or improve the reliability of the seal formed by the seal element against the interior surface of the socket.

BRIEF DESCRIPTION OF THE DRAWINGS

The numerous other advantages, features and functions of embodiments of an adjustable seal system will become clear and better understood in view of the following description, appended claims, and accompanying drawings. The following description is not intended to limit the scope of the adjustable seal system, but instead merely provides exemplary embodiments for ease of understanding.

FIG. 4 is a partial cross section of a seal component in an elevational view according to another embodiment.

FIG. 5 is a partial cross section of a seal component in an elevational view according to another embodiment.

FIG. 6 is a partial cross section of a seal component in an elevational view according to another embodiment.

FIG. 7 is a perspective view of a seal component according to another embodiment.

FIG. 8 is a partial cross section of the seal component shown in FIG. 7 in an elevational view.

FIG. 9 is a partial cutaway of the seal component shown in FIG. 7 in a perspective view.

FIG. 10 is a detailed perspective view of the seal component according to another embodiment.

Figure 1:
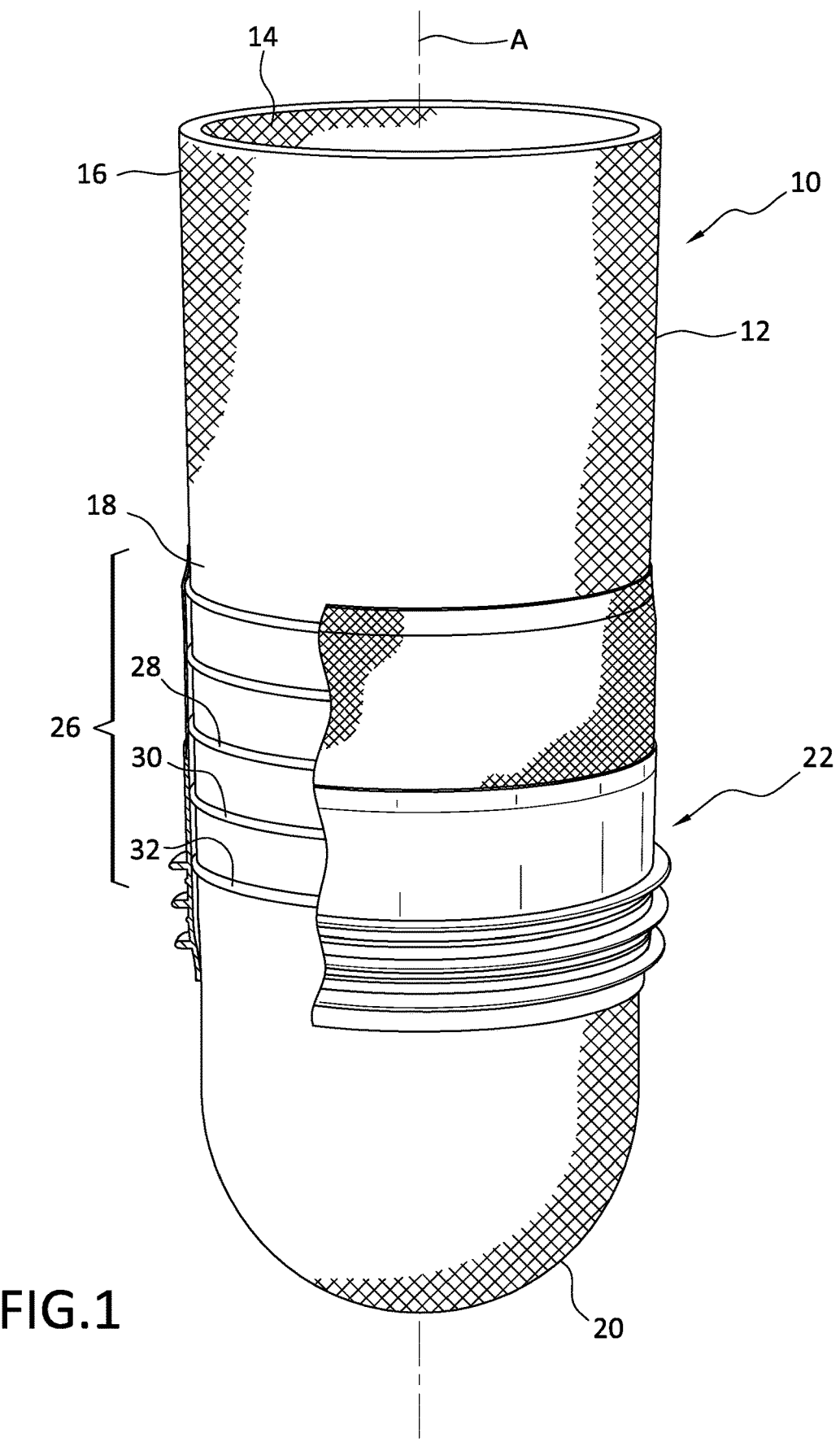
FIG. 1 is a perspective view showing an embodiment of a prosthetic liner having a movable adjustable seal system according to the disclosure.

The drawing figures are not necessarily drawn to scale, but instead are drawn to provide a better understanding of the components, and are not intended to be limiting in scope, but to provide exemplary illustrations. The figures illustrate exemplary configurations of an adjustable seal system, and in no way limit the structures or configurations of an adjustable seal system and components according to the disclosure.

DETAILED DESCRIPTION OF VARIOUS EMBODIMENTS

A better understanding of different embodiments of the invention may be had from the following description read in conjunction with the accompanying drawings in which like reference characters refer to like elements.

In each of the embodiments discussed herein, the suspension or prosthetic liner is intended for use between a residual limb and a prosthesis, such as a hard socket, and to be air-tight when donned over a residual limb. The inner surface of the prosthetic liner may be formed of a layer of silicone elastomer, thereby serving as a skin surface.

Silicone is advantageous and exemplary in that it allows for different levels and softness and strength to be incorporated into the liners of the present application. Moreover, silicone permits the addition of selected supplements, such as petroleum jelly and/or Aloe vera, which improve skin care and comfort. The suspension liner, however, can be constructed from a variety of other materials other than from silicone, and the embodiments herein are not limited to suspension liners formed from silicone.

An elasticity-controlling matrix material may be provided on the exterior of the prosthetic liner, the elasticity-controlling matrix material preferably being relatively compliant in a radial direction and substantially rigid or inelastic in an axial direction. The matrix material may extend over the distal or external side of the prosthetic liner and is advantageous in that it prevents movement of the prosthetic liner when a prosthesis, such as a socket, is worn thereover.

A prosthetic liner in accordance with this disclosure may be fabricated in enough sizes to accommodate various sizes of residual limbs. In use, a liner of the type described herein is rolled up from the proximal to the distal end, placed over the distal end of the residual stump and rolled back up or "donned" over the stump like a stocking. This procedure and the benefits achieved thereby are described in detail in U.S. Pat. No. 4,923,474, granted on May 8, 1990 and incorporated herein by reference. In addition, any of the prosthetic liners and sleeves mentioned herein may be constructed in the manner prescribed by U.S. Pat. No. 4,923,474. The embodiments of the prosthetic liner of the present application may be constructed according to the molding methods described in U.S. Pat. No. 6,485,776, granted on Nov. 26, 2002 and the entirety of which is incorporated herein by reference.

In use, a prosthetic liner carrying a seal component is worn on a residual limb and stepped into a prosthetic socket. As the residual limb is placed into the socket, the seal component forms an airtight seal with an interior surface of the socket and urges air out of the distal end of the socket through a distally positioned expulsion valve. When it is desired to release the connection between the prosthetic liner and the socket, the valve is released to allow a return to atmospheric or ambient pressure, and the residual limb and prosthetic liner can be removed from the socket.

When sealing against a socket, it should be kept in mind that the vacuum is formed between the seal component and the distal end of the socket; generally, no vacuum is created proximal of the seal between the prosthetic liner and the socket. Depending on configurations of the seal component, the seal component may not completely press against the socket wall, but rather only portions of the seal component press against the socket wall. For example, seal rings of the seal component may press against the socket wall, but portions, such as regions coaxial with and between the seal rings may not touch the socket wall.

Pressure is inversely proportional to the suspension force needed or provided to ensure stability and rotational control. The seal component preferably forms a hypobaric sealing membrane that conforms to the shape of the internal socket wall, providing an airtight seal between the prosthetic liner and the socket. Thus, the lower the pressure (or in other words, the greater the vacuum) between the seal component and the socket wall, the greater the suspension that is generated. It is often desirable that even pressure exists around the seal component in the connection between the socket and prosthetic liner. There is preferably firm suspension among the prosthetic liner, socket, and residual limb.

In observing FIG. 1, a prosthetic liner 10 includes a liner body 12 defining an internal cavity 14 for receiving a residual limb. The liner body 12 preferably has an elongate, generally conical shape, and defines a longitudinal axis A which extends between proximal and distal portions 16, 20. The proximal and distal portions 16, 20 are spaced apart by a middle portion 18. The liner body 12 may be formed from at least one material segment that is at least radially elastically extensible from a relaxed non-extended condition.

A seal component 22 is securable to an outer surface of the liner body 12 among an at least one seal band 26 formed along the outer surface of the liner body. 12 In this embodiment, the at least one seal band 26 defines at least three seal bands 28, 30 and 32 located about a circumference of the middle portion 18. The seal bands 28, 30, 32 may be formed from a fictional material to maintain the seal component 22 on the prosthetic liner 10. An example of a frictional material is silicone, however other suitable materials may be used. The seal component 22 frictionally fits against at least one of the seal bands 28, 30, 32 along a length of the liner body 12 and can be installed among any one of the seal bands 28, 30, 32. The seal component 22 can likewise be removed from the liner body 12 and readjusted as considered necessary at a new location. In other embodiments, the seal component 22 can be arranged to frictionally fit against a liner body 12 without any of the seal bands 28, 30, 32. For instance, the seal component 22 can be arranged to frictionally fit against a prosthetic liner comprising a textile-free prosthetic liner then for example the length of a liner sealing portion described below can be much shorter.

The seal component 22 is considered detachable in that it can be removed from the liner body 12, and adjustable to be repositioned on the liner body 12 without any adhesive or permanency. According to a desired height of the seal component 22 along the axis A of the liner body 12, the seal component 22 can be installed among any one or more of the seal bands 28, 30, 32.

According to the present disclosure, the seal component 22 includes a body having an outer surface defining a socket sealing portion arrange to engage with and form an airtight seal with an interior surface of the socket. An inner surface of the body defines a liner sealing portion extending in a proximal direction from an end of the socket sealing portion on the outer surface of the body. The liner sealing portion is arranged to frictionally engage and seal with the outer surface of the liner body 12, including at least one of the seal bands 28, 30, 32 to secure the seal component 22 on the liner body 12.

The liner sealing portion and the socket sealing portion are defined on different parts of the seal component 22. For instance, the liner sealing portion can extend between the end of the socket sealing portion and a proximal end of the body. It has been found that one source of undesirable migration of movable seal components between the socket and the prosthetic liner is that a sealing length of the liner sealing portion along the inside of the seal component in relation to a sealing length of the socket sealing portion along the outside of the seal component is typically too short, and thus the amount of traction between the socket and seal component tends to overcome the amount of traction between the seal component and the prosthetic liner, causing the seal component to migrate or undesirably move between the socket and the prosthetic liner. As used herein, traction generally refers to the amount of force a body can apply to a surface or another body before it slips.

In accordance with the present disclosure, then, the sealing length and/or position of the liner sealing portion is selectively configured in relation to the socket sealing portion to vary the traction at the inner and outer surfaces of the seal component 22. For instance, the liner sealing portion can comprise a sealing length of between about 25 mm and about 35 mm. Such a sealing length can provide an amount of traction along the inner surface of the seal component 22 that is neither too low nor too concentrated, accomplishing a secure suspension of the prosthetic liner 10 and residual limb within the socket that avoids unwanted migration of the seal component 22 without making the seal component 22 uncomfortable to use or difficult to don/doff.

This has the effect of reducing the likelihood of pressure points and/or unwanted movement between the liner body 12 and the seal component 22, making prosthetic suspension more comfortable and reliable. Such a sealing length along the liner sealing portion also can facilitate donning and doffing of the seal component 22 and limit unwanted bunching of the seal component 22. If the amount of traction at the outer surface of the seal component 22 substantially exceeds the amount of traction at the inner surface, movement of the seal component 22 with the socket may generate shear forces that cause the liner sealing portion to slip relative to the prosthetic liner 10, which, in turn, can cause unwanted bunching or movement of the seal component 22 on a liner body 12. Conversely, if the amount of traction between the seal component 22 and the prosthetic liner 10 is too great, it can make donning and doffing of the seal component 22 too strenuous and inconvenient. The seal component 22 thus allows for more reliable suspension of a residual limb within a socket and reduces the likelihood of the seal component 22 undesirably migrating between the prosthetic liner 10 and the socket during use.

Figure 2:
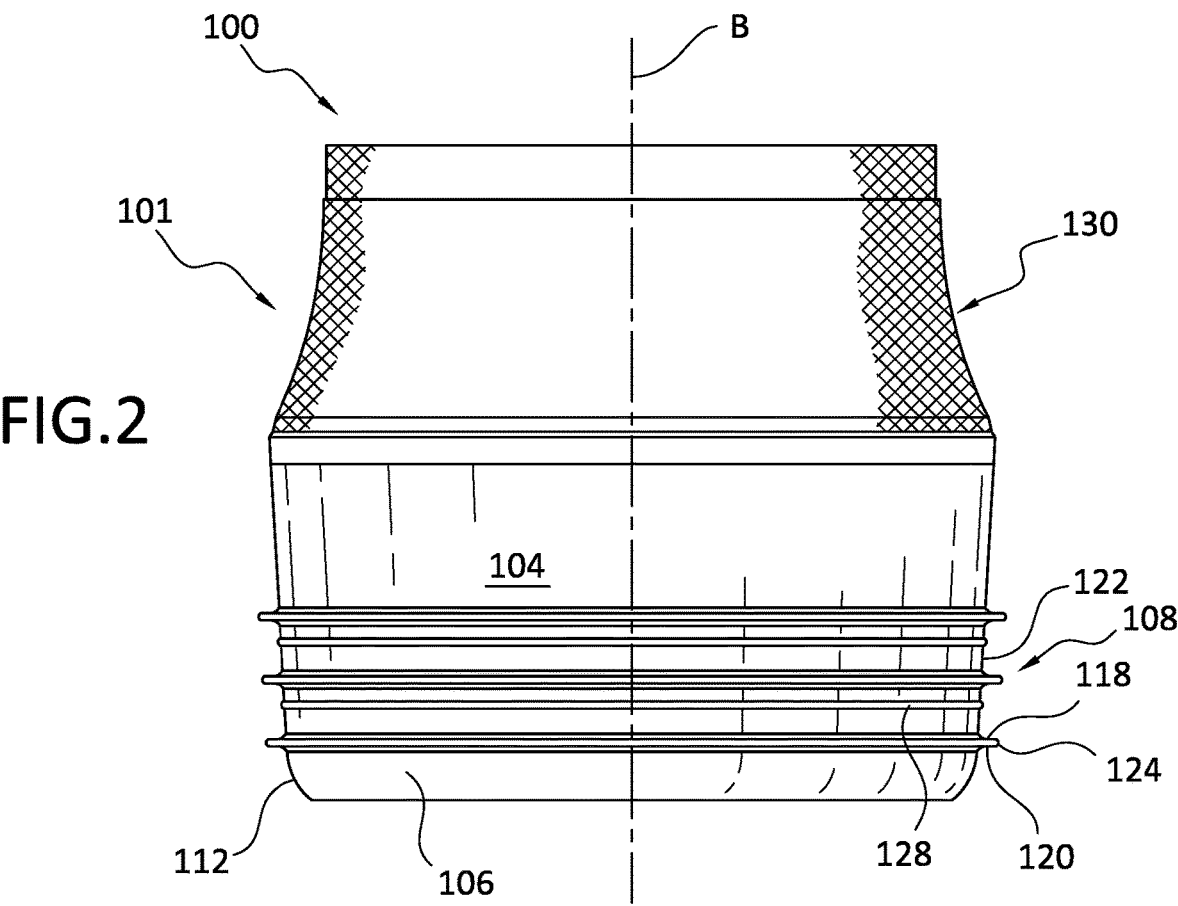
FIG. 2 is an elevational view of a seal component according to an embodiment.
Figure 3:
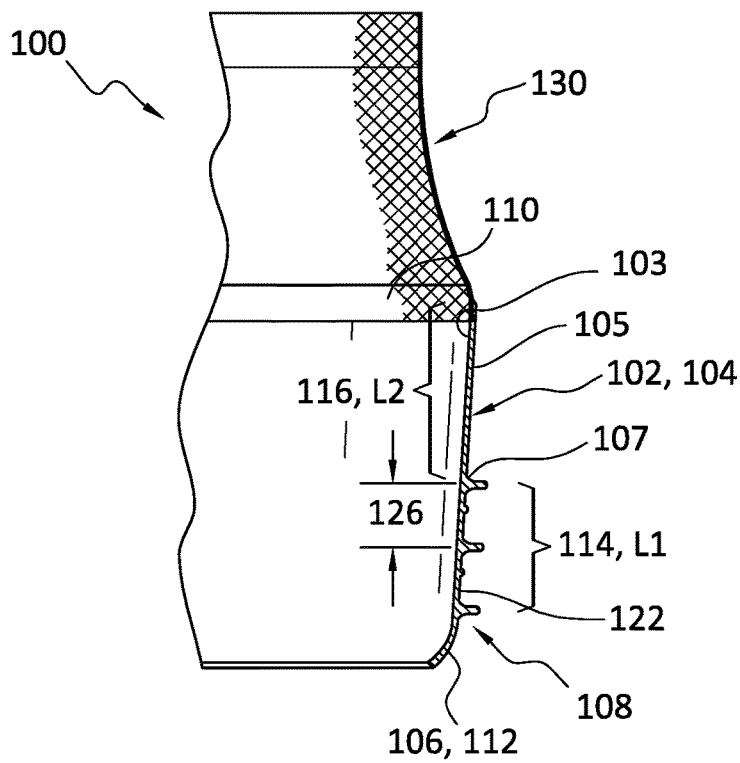
FIG. 3 is a partial cross section of the seal component shown in FIG. 2 in an elevational view.

FIGS. 2 and 3 show an adjustable seal system 100 comprising seal component 101 according to an embodiment of the present disclosure. The seal component 101 defines a body 102 having open upper and lower ends defining an opening therethrough and an inner surface 103 extending about an axis B and arranged to abut a surface of a liner body (e.g., the liner body 12). While the body 102 is shown and described including an open lower end, it will be appreciated that the open lower end can be omitted from any seal component of the present disclosure. For instance, the body 102 can include an open upper end and a closed lower end.

The body 102 can include an upper section 104 and a lower section 106. The upper portion 104 is arranged to be generally concentric with a liner body and can have a substantially uniform diameter along its length or height. The lower portion 106 defines a curvature 112 toward its lower end that decreases an inner diameter of the seal component 101. This allows the lower end 106 to compress against a liner body when the seal component 101 is donned thereon, advantageously helping to minimize unwanted relative movement between the seal component 101 and the liner body.

A plurality of seal elements 108 are located along an outer surface 105 of the seal component 101. The seal elements 108 protrude radially outward from a body profile 122 and are arranged for engagement with an interior surface of a socket.

As seen in the illustrated embodiment, the seal elements 108 collectively define a socket sealing portion 114 arranged to form a seal or attachment between the seal component 101 and the interior surface of the socket, providing resistance to axial and/or rotational movement between the seal component 101 and the socket during use. The socket sealing portion 114 defines a sealing length L1 that at least in part defines the amount of traction between the outer surface 105 of the seal component 101 and the interior surface of the socket. For instance, a decrease in the sealing length L1 can decrease the traction between the seal component 101 and the interior surface of the socket, and an increase in the sealing length L1 can increase the traction between the seal component 101 and the interior surface of the socket.

The inner surface 103 of the seal component 101 defines a liner sealing portion 116 extending in a proximal direction from an end 107 of the socket sealing portion 114 on the body 102. The liner sealing portion 116 is configured to provide a sealing interface between the inner surface 103 of the body 102 and the outer surface of the prosthetic liner.

The liner sealing portion 116 can define a sealing length L2 generally extending between a proximal edge on the body 102 and the end 107 of the socket sealing portion 114. The proximal edge on the body 102 can comprise an upper end 110 of the body 102. The sealing length L2 at least in part defines the amount of traction between the outer surface of the prosthetic liner and the inner surface 103 of the seal component 101.

For example, a decrease in the sealing length L2 can decrease the amount of traction between the seal component 101 and the outer surface of the prosthetic liner, and an increase in the sealing length L2 can increase the amount of traction between the seal component 101 and the outer surface of the prosthetic liner. In an embodiment, the sealing length L2 of the liner sealing portion 116 can be arranged to span a distance between at least two seal bands on the prosthetic liner and to engage therewith. As such, the sealing length L2 of the liner sealing portion 116 can be selectively configured in relation to a distance between at least two seal bands on the prosthetic liner to vary the traction at the inner surface 103 of the seal component 101. For instance, the sealing length L2 of the liner sealing portion 116 can be between about 1 and about 1.4 times (e.g., about 1.2 times) greater than a distance between at least two seal bands on the prosthetic liner, ensuring sufficient traction and sealing between the seal component 101 and the prosthetic liner. In an embodiment, the sealing length of the liner sealing portion 116 can be between about 28 mm and about 32 mm (e.g., about 30 mm) and the distance between at least two seal bands on the prosthetic liner that the liner sealing portion 116 is arranged to span and engage with can be about 25 mm. In other embodiments, the sealing length of the liner sealing portion 116 can be between about 24 mm and about 26 mm (e.g., about 25 mm) and the distance between at least two seal bands on the prosthetic liner that the liner sealing portion 116 is arranged to span and engage with can be about 20 mm. In other embodiments, the sealing length L2 of the liner sealing portion 116 can be arranged to span across at least one seal band and to engage therewith.

As seen, the liner sealing portion 116 and the socket sealing portion 114 are formed on different parts of the seal component 101. For example, the liner sealing portion 116 and the socket sealing portion 114 can be offset along the axis B of the seal component 101. It has been found that the traction along the socket sealing portion 114 between the seal elements 108 and the interior surface of the socket can cause a region of the inner surface 103 opposite the socket sealing portion 114 to tend to move away from the outer surface of the prosthetic liner, reducing the amount of traction and increasing the among of air leaking or escaping between the inner surface 103 of the seal component 101 and the prosthetic liner, and accordingly increasing the likelihood of slippage between the seal component 101 and the prosthetic liner. Due to the separation of the liner sealing portion 116 from the socket sealing portion 114 on the seal component 101 in embodiments of the present disclosure, the operation of the socket sealing portion 114 is less likely to directly influence the operation of the liner sealing portion 116. This advantageously allows for sufficient traction to be generated along the socket sealing portion 114, without directly affecting the strength or operation of the traction generated along the liner sealing portion 116.

According to the present disclosure, the sealing length L2 and/or position of the liner sealing portion 116 is selectively configured in relation to the socket sealing portion 114 to vary the traction at the inner and outer surfaces 103, 105 of the seal component 101. For instance, the sealing length L2 of the liner sealing portion 116 can be selected based on the sealing length L1 of the socket sealing portion 114. In an embodiment, the sealing length L2 of the liner sealing portion 116 can be between about 1.2 and about 1.3 times greater than the sealing length L1 of the socket sealing portion 114.

This is advantageous because if the amount of traction at the outer surface 105 of the seal component 101 substantially exceeds the amount of traction at the inner surface 103, movement of the seal component 101 with the socket may generate shear forces that cause the seal component to slip, which, in turn, can cause unwanted bunching or movement of the seal component 101 on a liner body. Conversely, if the amount of traction along the inner surface 103 is too great it can make donning and doffing of the seal component 101 too strenuous and inconvenient. Further, if the amount of traction along the inner surface 103 of the seal component 101 is too low or too concentrated, pressure points and/or unwanted movement between the liner body and the seal component 101 may develop, making prosthetic suspension uncomfortable and/or unreliable.

In other embodiments, the sealing length L2 of the liner sealing portion 116 can be between about 0.9 and 1.6, between about 1 and 1.5, or between about 1.1 and 1.4 times greater than the sealing length L1 of the socket sealing portion 114. In other embodiments, the sealing length L1 of the socket sealing portion 114 can be between about 22 mm and 27 mm (e.g., about 25 mm) and the sealing length L2 of the liner sealing portion 116 can be between about 28 mm and 32 mm (e.g., about 30 mm). It will be appreciated that in other embodiments the relationship between the sealing lengths of the liner sealing portion 116 and the socket sealing portion 114 can be greater or lower. For instance, the sealing length L2 of the liner sealing portion 116 can be shorter if there is less distance between adjacent seal bands on a prosthetic liner. In an embodiment, a sealing length L2 of the liner sealing portion 116 for use with a prosthetic liner including seal bands spaced apart by about 20 mm can be shorter than a sealing length L2 of the linear sealing portion 116 for use with a prosthetic liner including seal bands spaced about by about 25 mm.

In an embodiment, the sealing length L2 of the liner sealing portion 116 is preferably between about 25 mm and about 35 mm (e.g., about 30 mm). This provides an amount of traction along the inner surface 103 of the seal component 101 that can substantially maintain the position of the seal component 101 on a prosthetic liner when a typical amount of traction for suspending the socket is present along the socket sealing portion 114, reducing the likelihood of undesirable migration of the seal component 101 and improving reliability of the attachment formed by the seal component 101 between the prosthetic liner and the socket.

This sealing length L2 is also not too concentrated such as would form pressure points on a residual limb, thereby improving user comfort. It is also not too great or extensive, thereby reducing the likelihood of the traction along the liner sealing portion 116 overcoming the amount of traction along the socket sealing portion 114, and improving the reliability of the attachment formed by the seal component 101 between the prosthetic liner and the socket. Additionally, a sealing length L2 of between about 25 mm and about 30 mm along the liner sealing portion 116 is not too great to make manual movement of the seal component 101 on the prosthetic liner by a user too difficult, facilitating donning and doffing of the seal component 101. In other embodiments, the sealing length L2 can be between about 26 mm and 34 mm, about 27 mm and 33 mm, or about 29 mm and 31 mm. It will be appreciated that the sealing length L2 can be greater or smaller in other embodiments.

It will be appreciated that the amount of traction generated along the socket sealing portion 114 can be at least in part defined by the configuration of the seal elements 108. As such, the socket sealing portion 114 can define a greater traction with a shorter sealing length L1 based on the form of the seal elements 108. The sealing length L2 of the liner sealing portion 116 can thus be configured in relation to the configuration of the seal elements 108. This has the effect of reducing the likelihood of problems that can result when the traction generated by the structure of the seal elements 108 overrides the traction generated along the liner sealing portion 116, as previously discussed; for example, the unwanted bunching or migration of the seal component 101 along the prosthetic liner can be avoided.

The structure of the seal elements 108 will now be described in greater detail according to an embodiment. The seal elements 108 can have a resilient configuration extending in a distal direction from the end 107 and protruding radially from a body profile 122 of the seal component 101. Each of the seal elements 108 includes proximal and distal sections 118, 120 extending from the body profile 122 to a peak 124 defined as the outermost extending portion of the seal element 108. The proximal and distal sections 118, 120 can be generally parallel to one another and the peak 124 can be rounded.

The seal elements 108 are spaced apart from one another a gap 126 and are arranged to resiliently deflect toward the body profile 122 when the seal component 101 is donned on a liner body and placed within a socket. The seal elements 108 could be formed of the same material as the body 102 and created integrally in one piece with the body 102 during molding or forming of the body 102, or alternatively, could be formed of a softer or stiffer material or a material more suitable for a seal than the material forming the body, and then secured to the body 102. The seal elements 108 are shown comprising three seal elements 108 but can include any suitable number of seal elements.

In the illustrated embodiment, at least one grip ring 128 is formed on the body profile 122 in the socket sealing portion 114. The grip rings 128 can extend circumferentially about the body 102 and can comprise a plurality of grip rings 128 located between adjacent ones of the seal elements 108. The grip rings 128 are configured to grab the interior surface of the socket in the gaps 126 located between the seal elements 108. This advantageously can increase the amount of traction in the socket sealing portion 114 and reduce the likelihood of slippage in the gaps 126 between the seal elements 108.

The placement of the grip rings 128 in the gaps 126 between the seal elements 108 can help reduce interference from the grip rings 128 with the sealing function of the sealing elements 108. The grip rings 128 can be formed of a frictional material and can have a rounded cross-sectional shape. In other embodiments, the grip rings 128 can have a rectangular, trapezoidal, wave, or other cross-sectional shape. The grip rings 128 can be formed of a same or different material as the seal component 101.

The grip rings 128 have a radially short configuration in relation to the seal elements 108 such that the seal elements 108 significantly extend beyond the grip rings 128 in a radial direction relative to the axis B. More particularly, the seal elements 108 can have a height defined between the body profile 122 and the peak 124, and the grip rings 128 can have a height defined between the body profile 122 and an outer radial limit of the grip ring 128. In an embodiment, the height of at least one of the seal elements 108 can be more than about 4 or about 5 times the height of at least one of the grip rings 128.

The grip rings 128 can also be configured to maintain the position of the peaks 124 of the seal elements 108 away from the body profile 122 when the seal elements 108 deflect toward the body profile 122. For instance, the grip rings 128 can be positioned in the gaps 126 such that as the peak 124 of a seal element 108 resiliently deflects toward the body profile 122, the proximal section 118 or distal section 120 of the seal element 108 engages with at least one of the grip rings 128 before reaching the body profile 122, maintaining the peak 124 a distance radially from the body profile 122.

This advantageously can decrease the likelihood of the seal elements 108 sticking to or flattening out against the body profile 122 when the seal component 101 is inserted into a socket, which can undesirably restrict movement of the seal element 108 relative to the body 102 and can compromise the seal formed by the seal element 108 against the interior surface of the socket. The grip rings 128 can thus help increase the amount of traction along the socket sealing portion 114 and/or improve the reliability of the seal formed by the seal element 108 against the interior surface of the socket.

It will be appreciated that in other embodiments the amount of traction at the socket sealing portion 114 and/or the liner sealing portion 116 can be controlled by varying materials, surface treatments, and/or texturing of the body 102 and/or seal elements 108. For instance, the socket sealing portion 114 can be treated with a low friction coating. In other embodiments, the socket sealing portion 114 can be treated with Easy Glide®.

Optionally, a textile sleeve 130 can be secured to the upper portion 104 of the seal component 101 and arranged to radially compress against the outer surface of the liner body. The textile sleeve 130 is preferably an anatomically conforming fabric. The textile provides an interface for griping, and thereby minimizing fine hand movement needed to don and adjust the seal component 101 over the prosthetic liner. The sleeve 130 is preferably more flexible and elastic than the seal component 101 such that the sleeve 130 retracts to an original size upon release of tension of the sleeve 130, further minimizing the risk of unwanted migration while not impeding donning/doffing of the seal component 101.

The sleeve 130 has a diameter less than a diameter of the liner body at the distal portion of the sleeve 130 such that the sleeve 130 stretches over and is tensioned when selectively placed over the outer surface of the liner body. The sleeve 130 can include a main portion having a first elasticity, and a top band located at an upper end of the main portion and having a second elasticity. It will be appreciated that any of the seal components of the present disclosure may optionally include a textile sleeve 130 as described herein.

FIG. 4 shows an adjustable seal system 200 according to another embodiment comprising a seal component 201 with a plurality of seal elements 208 and a liner sealing portion 216. The seal component 201 defines a body 202 having open upper and lower ends defining an opening therethrough and an inner surface 203 arranged to abut an outer surface of a liner body. The profile of the seal elements 208 includes curvilinear proximal and distal sections 218, 220 extending from a body profile 222 toward a rounded peak 224.

The seal elements 208 form a socket sealing portion 214 for sealing the sealing component 201 to a socket and the inner surface 203 defines the liner sealing portion 216 extending in a proximal direction from an end 207, which may be a proximal end, of the socket sealing portion 214 on the body 202. The liner sealing portion 216 is configured to provide a sealing interface between the seal component 201 and the liner body beyond the seal elements 208.

The socket sealing portion 214 defines a sealing length L3 that at least in part defines the amount of traction between an outer surface 205 of the seal component 201 and the interior surface of the socket. The liner sealing portion 216 defines a sealing length L4 that at least in part defines the amount of traction between the outer surface of the prosthetic liner and the inner surface 203 of the seal component 201. The sealing length L4 can be defined between a proximal edge on the body 202 and the end 207 of the socket sealing portion 216. The proximal edge of the body 202 can define an upper end 210 of the body 202.

Like in other embodiments, the sealing length L4 and/or position of the liner sealing portion 216 can be selectively configured in relation to the socket sealing portion 214 to vary the traction at the inner and outer surfaces 203, 205 of the seal component 201. For instance, the liner sealing portion 216 and the socket sealing portion 214 can be axially offset from one another on the body 202, reducing the likelihood of undesirable interface between the socket sealing portion 214 and the liner sealing portion 216.

In an embodiment, the sealing length L4 of the liner sealing portion 216 can be between 25 mm and about 35 mm (e.g., about 30 mm).

As in previous embodiments, this configuration of the liner sealing portion 216 can provide an amount of traction along the inner surface 203 of the seal component 201 that is sufficient to substantially maintain the position of the seal component 201 on a prosthetic liner when a typical amount of traction for suspending the socket is generated along the socket sealing portion 214, without being so concentrated or extensive that the seal component 201 creates discomfort from, e.g., pressure points, or difficulty in donning/doffing the seal component 201.

FIG. 5 shows an adjustable seal system 300 according to yet another embodiment comprising a seal component 301 with a plurality of seal elements 308 and a liner sealing portion 316. The seal component 301 defines a body 302 having open upper and lower ends defining an opening therethrough and an inner surface 303 arranged to abut a surface of a liner body. The seal elements 308 form a socket sealing portion 314 for sealing the sealing component 301 to a socket and the inner surface 303 defines the liner sealing portion 316 extending a proximal direction from an end 307 of the socket sealing portion 314 on the body 302. The liner sealing portion 316 is configured to provide a sealing interface between the seal component 301 and the liner body beyond the seal elements 308.

The socket sealing portion 314 defines a sealing length L5 that at least in part defines the amount of traction between an outer surface 305 of the seal component 301 and the interior surface of the socket. The liner sealing portion 316 defines a sealing length L6 that at least in part defines the amount of traction between the outer surface of the prosthetic liner and the inner surface 303 of the seal component 301. The liner sealing portion 316 generally extends between the end 307 of the socket sealing portion 314 and a proximal edge on the body 302. The proximal edge on the body 302 can define an upper end 310 of the body 302.

The sealing length L6 and/or position of the liner sealing portion 316 can be selectively configured in relation to the socket sealing portion 314 to vary the traction at the inner and outer surfaces 30, 305 of the seal component 301. For instance, the liner sealing portion 316 and the socket sealing portion 314 may be axially offset from one another on the body 302, reducing the likelihood of undesirable interference between the socket sealing portion 314 and the liner sealing portion 316. In an embodiment, the sealing length L6 of a liner sealing portion 316 be between about 25 mm and about 35 mm to create and optimize a more reliable connection between a residual limb and the socket.

As seen in the illustrated embodiment, the profile of the seal elements 308 may be tapered from a distal end toward a proximal end to facilitate insertion of the seal component 301 into the socket and tends to resist outward movement of the seal component 301 from the socket. Also, the tapered form of the seal elements 308 can provide an increased sealing force between the seal component 301 and the socket when the seal component 301 is moved in a direction tending to withdraw it from the socket, or in other words the seal elements 308 seal more effectively when subjected to a pressure differential where a lower pressure exists towards the distal side of the seal element as compared to the proximal side thereof.

FIG. 6 shows an adjustable seal system 400 according to another embodiment comprising a seal component 401. The seal component 401 includes a single seal element 408 and a grip ring 428 positioned proximal of the seal element 408.

The seal element 408 and the grip ring 428 define a socket sealing portion 414 arranged to form a seal or attachment between the seal component 401 and the interior surface of the socket. The inner surface 403 of the seal component 401 defines a liner sealing portion 416 extending a proximal direction from an end 407 of the socket sealing portion 414 on the body 402. The liner sealing portion 416 is configured to provide a sealing interface between the inner surface 403 of the body 402 and the outer surface of the prosthetic liner beyond or proximal to the socket sealing portion 414.

The socket sealing portion 414 defines a sealing length L7 that at least in part defines the amount of traction between an outer surface 405 of the seal component 401 and the interior surface of the socket. The liner sealing portion 416 defines a sealing length L8 that at least in part defines the amount of traction between the outer surface of the prosthetic liner and the inner surface 403 of the seal component 401. The liner sealing portion 416 generally extends between the end 407 of the socket sealing portion 414 and a proximal edge on the body 402.

The sealing length L8 and/or the position of the liner sealing portion 416 can be selectively configured in relation to the socket sealing portion 414 to vary the traction at the inner and outer surfaces 403, 405 of the seal component 401. For example, in the embodiment of FIG. 6 the sealing length L8 is substantially greater than the sealing length L7 but also not too long to make manual movement of the seal component 401 on the prosthetic liner by a user too difficult, facilitating donning and doffing of the seal component 401 for a user.

The profile of the seal element 408 is shown defining an elongate rectangular shape but can define any suitable shape. The grip ring 428 can be arranged to provide additional traction between the seal component 401 and a prosthetic socket. The grip ring 428 can also be arranged to reduce the likelihood of the seal element 408 undesirably sticking to the body profile 422 during use, such as when the prosthetic liner is inserted into the socket.

FIGS. 7-9 show an adjustable seal system 500 according to another embodiment comprising a seal component 501. The seal component 501 defines a body 502 forming an inner surface 503 arranged to engage with a liner body. The body 502 includes an upper section 504 and a lower section 506.

A seal element 508 is attached to the outer surface 505 of the seal component 501 and arranged for engagement with an interior surface of a socket. The seal element 508 defines a socket sealing portion 514 arranged to create a seal or attachment between the seal component 501 and the interior surface of the socket that provides resistance to axial and/or rotational movement between the seal component 501 and the socket during use.

The inner surface 503 of the body 502 defines a liner sealing portion 516 extending in a proximal direction from an end 507 of the socket sealing portion 514 on the body 502 comprising a connection point 513 between the body 502 and the seal element 508. The liner sealing portion 516 is configured to provide a sealing interface between the inner surface 503 of the body 502 and the outer surface of the prosthetic liner.

The socket sealing portion 514 defines a sealing length L9 that at least in part defines the amount of traction between the seal component 501 and the interior surface of the socket. The liner sealing portion 516 defines a sealing length L10 that at least in part defines the amount of traction between the outer surface of the prosthetic liner and the inner surface 503 of the seal component 501. The sealing length L10 can be defined between a proximal edge on the body 502 and the connection point 513. The proximal edge can define an upper end 510 of the body 502.

The liner sealing portion 516 and the socket sealing portion 514 are defined on different parts of the seal component 501. In an embodiment, the liner sealing portion 516 is defined along the body 502 proximal to the connection point 513, and socket sealing portion 514 is defined on a member other than the body 502. For instance, the seal element 508 can comprise a member cantilevered from the connection point 513 on the body and separated from the body 502 by a variable space 530. The seal element 508 can thus freely flex relative to the body 502, and the liner sealing portion 516 and the socket sealing portion 514 are separated by the variable space 530. This physical separation of the liner sealing portion 516 from the socket sealing portion 514 on the seal component 501 reduces the likelihood of the undesirable interference between the socket sealing portion 514 and the liner sealing portion 516. This advantageously allows for traction to be generated along the socket sealing portion 514, without directly affecting the strength or operation of the traction generated along the liner sealing portion 516.

The sealing length L10 and/or position of the liner sealing portion 516 is selectively configured in relation to the socket sealing portion 514 to vary the traction at the inner and outer surfaces 503, 505 of the seal component 501. For instance, the sealing length L10 of the liner sealing portion 516 can be between 25 mm and about 35 mm (e.g., about 30 mm). This provides an amount of traction along the inner surface 503 of the seal component 501 that can substantially maintain the position of the seal component 501 on a prosthetic liner when a typical amount of traction for suspending the socket is present along the socket sealing portion 514, reducing the likelihood of undesirable movement or migration of the seal component 501 between the prosthetic liner and the socket, and improving reliability of the seal component 501. The sealing length of the liner sealing portion 516 is also not too short to generate pressure points on a residual limb, improving comfort of the seal component 501. In other embodiments, the sealing length L10 of the liner sealing portion 516 can be between about 30 mm and 45 mm, between about 33 mm and 42 mm, or between about 35 mm and about 40 mm (e.g., about 39 mm). The sealing length L9 can be between about 20 mm and about 34 mm, about 22 mm and about 30 mm, or about 25 mm and about 28 mm (e.g., about 27 mm). It will be appreciated that the sealing lengths L9, L10 can be greater or smaller.

The seal element 508 can be configured to vary the amount of traction along the socket sealing portion 514. For instance, the seal element 508 has a radially outermost portion, peak, or seal lip 524 arranged generally concentric with the upper portion 504. A lower segment 520 extends outwardly and in some embodiments conically from the connection point 513 to the seal lip 524.

An upper segment 518 extends inwardly from the seal lip 524 toward the upper portion 504 of the body 502. A variable space 530 is defined between the body 502 and the upper segment 518 such that the seal element 508 is arranged to be compressed against a body profile 522 of the upper portion 504 when the seal component 501 is inserted in a socket. A flap 532 extends from the upper segment 518 and may be oriented generally parallel with the upper portion 504 and is spaced from the upper portion 504 by the variable space 530. It will be appreciated that socket sealing portion 514 can move relative to the liner sealing portion 516 to compensate for volume changes in the residual limb. The lower segment 520 defines at least one radial seal 532, 534 that, in combination with the seal lip 524, are arranged to maintain connection with an interior socket wall, thereby creating a seal between the seal component 501 and the socket.

The body profile 522 defines one or more raised portions 540 radially positioned between the seal element 508 and the body 502. In an embodiment, the one or more raised portions 540 are radially positioned between the seal element 508 and the upper portion 504 and are sized and configured to create channels for airflow between the upper portion 504 and the seal element 508 during use. More particularly, the one or more raised portions 540 can be configured such that when the seal element 508 is compressed against the body 502 during donning or loading of the prosthetic liner within the socket, closing the variable space 530 toward the body profile 522, the seal element 508 engages with the one or more raised portions 540 before reaching the body profile 522, maintaining at least a portion of the seal element 508 a distance from the body profile 522.

This distancing or spacing of the seal element 508 from the body profile 522 provided by the raised portions 540 can create channels between the body 502 and the seal element 508 for permitting airflow therebetween. This advantageously reduces the risk of the seal element 508 sticking or becoming stuck on the body profile 522, which can undesirably restrict movement of the seal element 508 relative to the body 502 and can compromise the seal formed by the seal element 508 against the interior surface of the socket, especially during use of the prosthesis, such as a leg or foot. The one or more raised portions 540 can thus help increase the amount of traction along the socket sealing portion 514 and/or improve the reliability of the seal formed by the seal element 508 against the interior surface of the socket. It will be appreciated that the channels formed by the raised portions 540 between the body profile 522 and the seal element 508 can be around and/or between the one or more raised portions 540.

The one or more raised portions 540 can also provide rotation control between the seal element 508 and the body 502, reducing the likelihood of undesirable rotational issues. For instance, the one or more raised portions 540 can be configured to frictionally or mechanically grip the inner side of the seal element 508 to limit relative rotation between the seal element 508 and the body 502.

The one or more raised portions 540 can define a variety of shapes such as bubble, dome, arcuate, semi-hemispherical, square, and other available shapes that may be molded on the body 502. In the illustrated embodiment, the one or more raised portions 540 comprise a single protrusion on the body profile 522. In other embodiments, the one or more raised portions 540 can comprise three linear protrusions 540A, 540B, and 540C as shown in FIG. 10 or any other suitable number or shape of raised portions. For instance, it will be appreciated that the one or more raised portions 540 can extend generally parallel to an axis C and/or obliquely relative to the axis C. The raised portions 540 can be comprise linear protrusions, curved protrusions, or both. The raised portions 540 can comprise coil protrusions or can extend in a cross-hatch or mesh pattern between the seal element 508 and the body 502.

The raised portions 540 can extend along the entirety or part of the height of the body 502. For instance, the raised portions 540 can define a length generally corresponding to the flap 532. The raised portions 540 can extend downwardly from the top or proximal edge 510 of the body 502. It will be appreciated that any suitable seal component of the present disclosure may optionally include one or more raised portions 540 as described herein.

Figure 11:
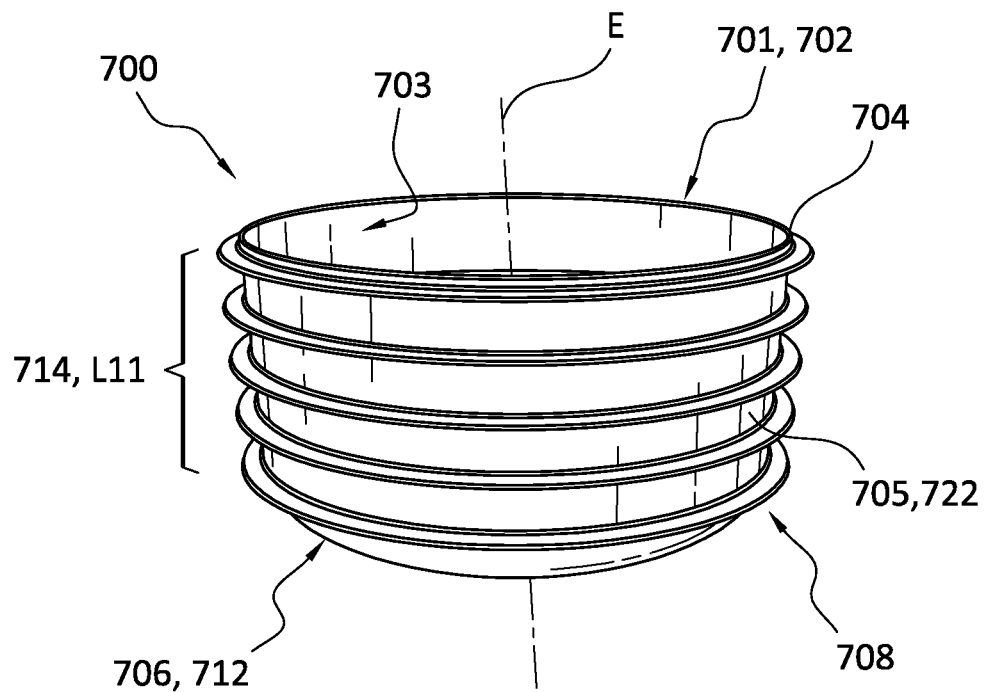
FIG. 11 is a perspective view of a seal component according to another embodiment.
Figure 12:
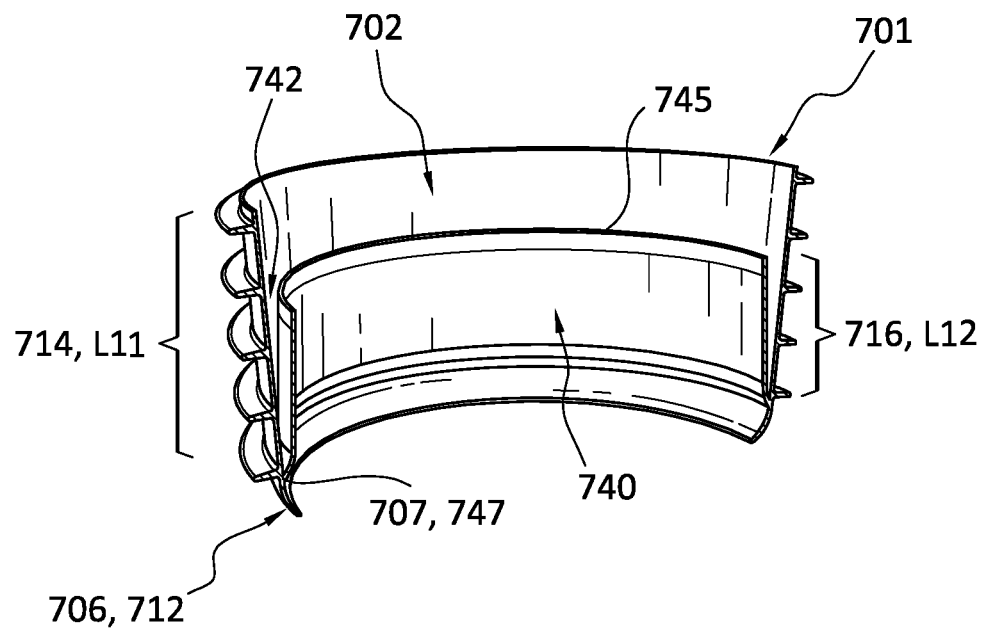
FIG. 12 is a cross section of the seal component shown in FIG. 11 in a perspective view.
Figure 13:
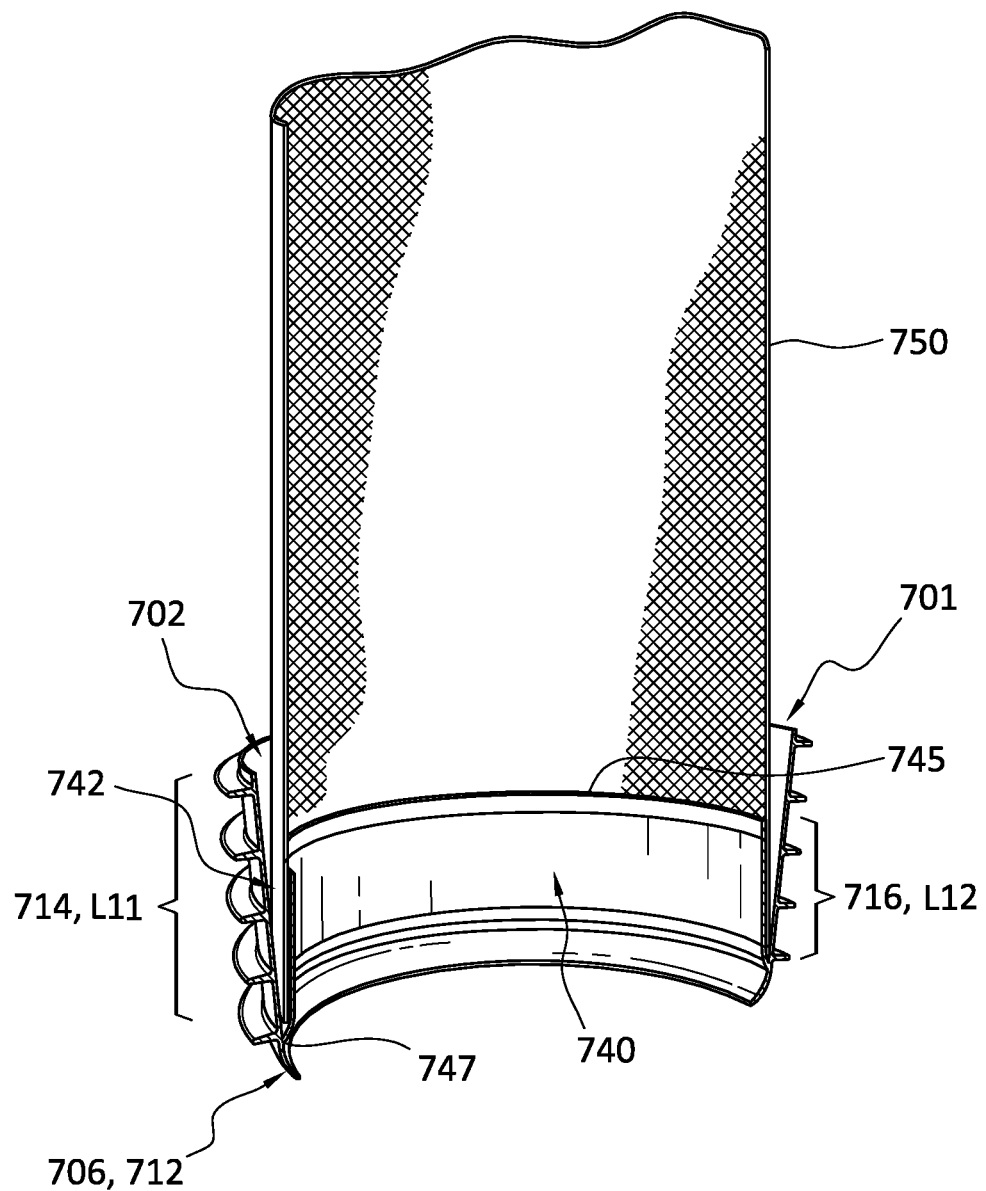
FIG. 13 is another cross section of the seal component shown FIG. 11 in a perspective view including a prosthetic sock.

FIGS. 11-13 show yet another embodiment of an adjustable seal system 700 comprising a seal component 701 including a body 702 forming an inner surface 703 extending about an axis E and arranged to abut an outer surface of a liner body (e.g., liner body 12). The body 702 includes an upper section 704 and a lower section 706. The upper portion 704 is arranged to be generally concentric with the liner body and can have a substantially uniform diameter along its length of height. The lower section 706 defines a curvature 712 toward its lower end that decreases an inner diameter of the seal component 701. This curvature 712 allows the lower end to compress against the liner body when the seal component 701 is donned thereon, advantageously helping to minimize unwanted relative movement between the seal component 701 and the liner body.

A plurality of seal elements 708 are formed along an outer surface 705 of the body 702. The seal elements 708 protrude radially outward from a body profile 722 and are arranged for engagement with a socket wall. The seal elements 708 are shown comprising five seal rings arranged for deflection and are axially spaced along the body profile 722 but can include any suitable number and/or structure of seal elements.

The seal elements 708 form a socket sealing portion 714 for sealing the sealing component 701 to a socket and the inner surface 703 defines a liner sealing portion 716 that provides a sealing interface between the seal component 701 and the liner body.

The liner sealing portion 716 and the socket sealing portion 714 are defined on different parts of the seal component 701. For instance, the socket sealing portion 714 is defined along the body profile 722 and the liner sealing portion 716 is defined on a separate interior wall 740 having an upper free end 745 and a lower end 747 connected to the lower section 706 on the inner surface 703 of the body 702. More particularly, the liner sealing portion 716 is defined along the radial inner surface of the interior wall 740. The lower end 747 of the interior wall 740 can comprise an end 707 of the socket sealing portion 714.

A variable space 742 is defined between the body 702 and the interior wall 740 such that the interior wall 740 is arranged to be compressed against the body 702 when the seal component 701 is donned on a prosthetic liner filling, reducing, or eliminating variable space 742. The interior wall 740 can thus freely move or pivot relative to the body 702, and the liner sealing portion 716 and the socket sealing portion 714 are separated by the variable space 742. This reduces the likelihood of undesirable interference between the socket sealing portion 714 and the liner sealing portion 716 and allows for traction to be generated along the socket sealing portion 714, without directly affecting the strength or operation of the traction generated along the liner sealing portion 716.

The socket sealing portion 714 defines a sealing length L11 that at least in part defines the amount of traction between the seal component 701 and the interior surface of the socket. The liner sealing portion 716 defines a sealing length L12 that at least in part defines the amount of traction between the seal component 701 and the outer surface of the prosthetic liner. The sealing length L12 can be defined between an end 707 of the socket sealing portion 714 and a proximal edge on the body 702. For instance, the proximal edge on the body 702 can comprise the upper free end 745 of the interior wall 740.

The sealing length L11 of the socket sealing portion 714 can be between about 60 mm and 80 mm, about 65 mm and 75 mm, or about 67 mm and 72 mm (e.g., 70 mm). This greater distance increases the area of the sealing interface between the seal component 701 and the socket, which, in turn, can more evenly distribute traction and is less likely to strangle, cut off circulation in, or otherwise create discomfort in a residual limb.

Like in other embodiments, the sealing length L12 and/or the position of the liner sealing portion 716 is selectively configured in relation to the socket sealing portion 714 to vary the traction at the inner and outer surfaces 703, 705 of the seal component 701. For instance, the sealing length of the liner sealing portion 716 can be between about 25 mm and about 35 mm. This configuration of the liner sealing portion 716 can provide an amount of traction along the inner surface 703 of the seal component 701 that is sufficient to substantially maintain the position of the seal component 701 on a prosthetic liner when a typical amount of traction for suspending the socket is generated along the socket sealing portion 714, reducing the likelihood of movement of the seal component 701 between the prosthetic liner and the socket, and improving reliability of the seal component 201.

Further, because the liner sealing portion 716 is on a different member that can move relative to the socket sealing portion 714, the seal component 701 can better compensate for volume changes in the residual limb to improve suspension of the adjustable seal component 701 over known adjustable seal components.

According to a variation, an open-ended prosthetic sock 750 or fabric sleeve having a distal portion can be positioned within the variable space 742 between the interior wall 740 and the inner surface 702 as shown in FIG. 13. This beneficially can provide cushioning and help locate the seal component 701 on the prosthetic liner to improve ease of use over known adjustable seal components. Moreover, the compression of the interior wall 740 against the inner surface 702 can secure the prosthetic sock 750 within the variable space 742, helping to maintain the prosthetic sock 750 in a proper position during use. It will be appreciated that any seal component of the present disclosure may optionally include an interior wall and/or open-ended prosthetic sock as described herein.

Other examples of adjustable seal components and prosthetic liners with seal bands can be found in U.S. Pat. Nos. 9,707,106, 9,603,726 and U.S. patent application Ser. No. 15/284,731, each owned by the assignee of the present disclosure and incorporated herein by reference. It will be appreciated that the socket sealing portion and/or liner sealing portion may be decided according to the needs of the user, and sensitive areas may be avoided. Moreover, in other embodiments, the adjustable seal components can be arranged to engage a liner body without any seal bands. For instance, the adjustable seal components can be arranged to engage with and secure on a liner comprising a textile free liner. The adjustable seal embodiments may enable improved durability by having better abrasion resistance due to the versatility in placement of the seal component and its separate yet non-permanent attachment to the liner.

The adjustable seal system, seal component, and method for using the same according to the present disclosure addresses problems in existing seal systems in that an adjustable seal is provided that can be removably mounted on a prosthetic liner and has a liner sealing portion configured to cooperate with a socket sealing portion to securely mount the adjustable seal on the prosthetic liner and to securely suspend the prosthetic liner and residual limb within the socket. The liner sealing portion is further advantageously configured to have a length sufficient to avoid unwanted migration of the adjustable seal without creation pressure points, discomfort, or difficulty in donning and doffing the adjustable seal component.

While the foregoing embodiments have been described and shown, alternatives and modifications of these embodiments, such as those suggested by others, may be made to fall within the scope of the invention. The principles described may be extended to other types of prosthetic devices.

It is to be understood that not necessarily all objects or advantages may be achieved under any embodiment of the disclosure. Those skilled in the art will recognize that the adjustable seal system may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of skill in this art to construct an adjustable seal system in accordance with principles of the present disclosure. It will be understood by the skilled artisan that the features described herein may apply to other types of orthopedic, prosthetic, or medical devices.

Although this disclosure describes certain exemplary embodiments and examples of an adjustable seal system, it nevertheless will be understood by those skilled in the art that the present disclosure extends beyond the specifically disclosed prosthetic socket embodiments to other alternative embodiments and/or users of the disclosure and obvious modifications and equivalents thereof. It is intended that the scope of the present disclosure should not be limited by the particular disclosed embodiments described above, and may be extended to prosthetic devices and supports, and other applications that may employ the features described herein.

The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. An adjustable seal system for providing an interface between a residual limb and a prosthetic socket, the adjustable seal system comprising:
 a prosthetic liner adapted to provide the interface between the residual limb and the prosthetic socket, the prosthetic liner defining a longitudinal axis and at least one seal band extending radially outwardly from an outer surface of the prosthetic liner and relative to the longitudinal axis;
 a seal component arranged for removably securing to the outer surface of the prosthetic liner and over the at least one seal band, the seal component including:
  a body having open upper and lower ends and an inner surface defining an opening therethrough, and an outer surface opposite the inner surface;
  a socket sealing portion on the outer surface of the body and arranged to engage and form an airtight seal with an interior surface of the prosthetic socket, the socket sealing portion arranged to extend distally of the at least one seal band relative to the longitudinal axis, the socket sealing portion defining at least one seal element formed on the outer surface of the body and extending radially outwardly therefrom relative to the longitudinal axis of the prosthetic liner, the socket sealing portion arranged to extend distally beyond the at least one seal band; and
  a liner sealing portion on the inner surface of the body arranged to frictionally engage and seal with the outer surface of the prosthetic liner, the liner sealing portion defining a sealing length extending in a proximal direction from a distal end of the socket sealing portion and terminating at a proximal edge on the body, the sealing length of the liner sealing portion being between about 25 mm and about 35 mm and selected in relation to the socket sealing portion to vary traction at the inner and outer surfaces of the body of the seal component, the liner sealing portion is arranged to correspond and extend over the at least one seal band;
 wherein the at least one seal element includes first and second seal elements formed on the outer surface of the body and radially protruding relative to an axis of the liner sealing portion and from a body profile of the body;

wherein at least one grip ring is formed on the body and extends circumferentially about the outer surface of the body, the at least one grip ring is located only in a gap defined between the first and second seal elements relative to the axis of the liner sealing portion;

wherein the at least one grip ring has a radially shorter configuration in relation to the first and second seal elements such that the first and second seal elements have a radially extending peak defined as an outermost portion of the first and second seal elements and extending beyond the at least one grip ring in a radial direction relative to the axis of the liner sealing portion;

wherein the at least one grip ring is configured to maintain a position of the radial peak of the first and second seal elements extending away from the body profile of the body when the first and second seal elements are deflected toward the body profile, the at least one grip ring is positioned in the gap such that as the peak of the first or second seal element resiliently deflects toward the body profile, a proximal section or a distal section of the first or second seal element engages the at least one of the grip ring before reaching the body profile, thereby maintaining the peak at a distance radially from the body profile.

2. The adjustable seal system of claim 1, wherein the sealing length of the liner sealing portion is about 30 mm.

3. The adjustable seal system of claim 1, wherein the sealing length of the liner sealing portion is between about 1.2 and 1.3 times greater than a sealing length of the socket sealing portion defined between the distal end of the socket sealing portion and the proximal edge on the body of the socket sealing portion.

4. The adjustable seal system of claim 1, wherein the first and second seal elements define proximal and distal sections extending toward the body profile from the peak, the peaks of the first and second seal elements are parallel to one another.

5. The adjustable seal system of claim 4, wherein the peak of the first and second seal elements is rounded.

6. The adjustable seal system of claim 1, wherein the first and second seal elements have a height defined between the liner sealing portion and the peak thereof, and the at least one grip ring has a height defined between the body profile and an outer radial limit of the at least one grip ring, the height of the first and second seal elements is more than about 4 or about 5 times the height of the at least one grip ring.

7. The adjustable seal system of claim 1, wherein the at least one grip ring is formed from a frictional material and has a rounded cross-sectional shape.

8. An adjustable seal system for providing an interface between a residual limb and a prosthetic socket, the adjustable seal system comprising:

a prosthetic liner adapted to provide the interface between the residual limb and the prosthetic socket, the prosthetic liner defining a longitudinal axis and at least one seal band extending radially outwardly from an outer surface of the prosthetic liner and relative to the longitudinal axis;

a seal component arranged for removably securing to the outer surface of the prosthetic liner and over the at least one seal band, the seal component including:

a body having open upper and lower ends and an inner surface defining an opening therethrough, and an outer surface opposite the inner surface;

a socket sealing portion on the outer surface of the body and arranged to engage and form an airtight seal with an interior surface of the prosthetic socket, the socket sealing portion arranged to extend distally of the at least one seal band relative to the longitudinal axis, the socket sealing portion defining at least one seal element formed on the outer surface of the body and extending radially outwardly therefrom relative to the longitudinal axis of the prosthetic liner, the socket sealing portion arranged to extend distally beyond the at least one seal band;

a liner sealing portion on the inner surface of the body proximal to the socket sealing portion and arranged to frictionally engage and seal on the outer surface of the prosthetic liner, the liner sealing portion defining a sealing length extending in a proximal direction from a distal end of the socket sealing portion on the body and terminating at the open upper end of the body, the sealing length of the liner sealing portion being between about 25 mm and about 35 mm and selected in relation to the socket sealing portion to vary traction at the inner and outer surfaces of the body of the seal component, the liner sealing portion is arranged to correspond and extend over the at least one seal band; and a textile sleeve secured to the upper end of the body, the textile sleeve being more flexible and elastic than the body, and the textile sleeve having a diameter less than a diameter of the prosthetic liner proximal of the at least one seal band;

wherein the at least one seal element includes first and second seal elements formed on the outer surface of the body and radially protruding relative to an axis of the liner sealing portion and from a body profile of the body;

wherein at least one grip ring is formed on the body and extends circumferentially about the outer surface of the body, the at least one grip ring is located only in a gap defined between the first and second seal elements relative to the axis of the liner sealing portion;

wherein the at least one grip ring has a radially shorter configuration in relation to the first and second seal elements such that the first and second seal elements have a radially extending peak defined as an outermost portion of the first and second seal elements and extending beyond the at least one grip ring in a radial direction relative to the axis of the liner sealing portion;

wherein the at least one grip ring is configured to maintain a position of the radial peak of the first and second seal elements extending away from the body profile of the body when the first and second seal elements are deflected toward the body profile, the at least one grip ring is positioned in the gap such that as the peak of the first or second seal element resiliently deflects toward the body profile, a proximal section or a distal section of the first or second seal element engages the at least one of the grip ring before reaching the body profile, thereby maintaining the peak at a distance radially from the body profile.

9. The adjustable seal system of claim 8, wherein the sealing length of the liner sealing portion is between about 1.2 and 1.3 times greater than a sealing length of the socket sealing portion defined between the distal end of the socket sealing portion and the proximal edge on the body of the socket sealing portion.

10. An adjustable seal system comprising:
a prosthetic socket;
a prosthetic liner adapted to provide an interface between a residual limb and the prosthetic socket, the prosthetic liner defining a longitudinal axis and at least one seal band extending radially outwardly from an outer surface of the prosthetic liner and relative to the longitudinal axis; and
a seal component arranged for removably securing to the outer surface of the prosthetic liner and over the at least one seal band, the seal component including:
a body having open upper and lower ends and an inner surface defining an opening therethrough, and an outer surface opposite the inner surface;
a socket sealing portion on the outer surface and arranged to engage and form an airtight seal with an interior surface of the prosthetic socket, the socket sealing portion arranged to extend distally of the at least one seal band relative to the longitudinal axis, the socket sealing portion defining at least one seal element formed on the outer surface of the body and extending radially outwardly therefrom relative to the longitudinal axis of the prosthetic liner, the socket sealing portion arranged to extend distally beyond the at least one seal band; and
a liner sealing portion on the inner surface of the body proximal to the socket sealing portion and arranged to frictionally engage and seal on the outer surface of the prosthetic liner, the liner sealing portion defining a sealing length extending in a proximal direction from a distal end of the socket sealing portion on the body and terminating at the open upper end of the body, the sealing length of the liner sealing portion being between about 25 mm and about 35 mm and selected in relation to the socket sealing portion to vary traction at the inner and outer surfaces of the body of the seal component, the liner sealing portion is arranged to correspond and extend over the at least one seal band;
wherein the at least one seal element includes first and second seal elements formed on the outer surface of the body and radially protruding relative to an axis of the liner sealing portion and from a body profile of the body;
wherein at least one grip ring is formed on the body and extends circumferentially about the outer surface of the body, the at least one grip ring is located only in a gap defined between the first and second seal elements relative to the axis of the liner sealing portion;
wherein the at least one grip ring has a radially shorter configuration in relation to the first and second seal elements such that the first and second seal elements have a radially extending peak defined as an outermost portion of the first and second seal elements and extending beyond the at least one grip ring in a radial direction relative to the axis of the liner sealing portion;
wherein the at least one grip ring is configured to maintain a position of the peak of the first and second seal elements extending away from the body profile of the body when the first and second seal elements are deflected toward the body profile, the at least one grip ring is positioned in the gap such that as the peak of the first or second seal element resiliently deflects toward the body profile, a proximal section or a distal section of the first or second seal element engages the at least one of the grip ring before reaching the body profile, thereby maintaining the peak at a distance radially from the body profile.

11. The adjustable seal system of claim 10, wherein the sealing length of the liner sealing portion is between about 1.2 and 1.3 times greater than a sealing length of the socket sealing portion defined between the distal end of the socket sealing portion and the proximal edge on the body of the socket sealing portion.

* * * * *